US011781169B2

(12) United States Patent
Grass et al.

(10) Patent No.: US 11,781,169 B2
(45) Date of Patent: Oct. 10, 2023

(54) ENZYMATIC DNA REPAIR

(71) Applicant: MICROSOFT TECHNOLOGY LICENSING, LLC, Redmond, WA (US)

(72) Inventors: Robert N. Grass, Zurich (CH); Alexander Xavier Christof Kohll, Zurich (CH); Weida Chen, Zurich (CH)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 119 days.

(21) Appl. No.: 16/152,808

(22) Filed: Oct. 5, 2018

(65) Prior Publication Data

US 2020/0109436 A1 Apr. 9, 2020

(51) Int. Cl.
*C12Q 1/6806* (2018.01)
*G06N 3/123* (2023.01)

(52) U.S. Cl.
CPC .......... *C12Q 1/6806* (2013.01); *G06N 3/123* (2013.01)

(58) Field of Classification Search
CPC .............................. G06N 3/123; C12Q 1/6806
See application file for complete search history.

(56) References Cited

U.S. PATENT DOCUMENTS

| | | |
|---|---|---|
| 2006/0014154 A1 | 1/2006 | Eshoo |
| 2006/0177867 A1 | 8/2006 | Evans et al. |
| 2010/0173364 A1* | 7/2010 | Evans, Jr. ............... C12Q 1/686 435/91.2 |
| 2018/0245072 A1 | 8/2018 | Raymond et al. |
| 2018/0253563 A1* | 9/2018 | Peck ...................... G16B 50/30 |

FOREIGN PATENT DOCUMENTS

WO 2018148257 A1 8/2018

OTHER PUBLICATIONS

Panda, DNA as a digital information storage device: hope or hype?, 3 Biotech, 8(5): 239, 2018. (Year: 2018).*
Sikorsky, Effect of DNA damage on PCR amplification efficiency with the relative threshold cycle method, Biochem Biophys Res Commun, 323: 823-830, 2004. (Year: 2004).*
Robertson, Assessing PreCR™ repair enzymes for restoration of STR profiles from artificially degraded DNA for human identification, Forensic Science International: Genetics, 12: 168-180, 2014. (Year: 2014).*
Datasheet for PreCR™ Repair Mix, New England BioLabs, 2015. (Year: 2015).*
Haughton, Repetition Coding as an Effective Error Correction Code for Information Encoded in DNA, 2011 IEEE 11th International Conference on Bioinformatics and Bioengineering, IEEE, pp. 253-260, 2011. (Year: 2011).*
Nguyen et al., "Long-Term Stability and Integrity of Plasmid-Based DNA Data Storage", In Journal of Polymers, vol. 10, Issue 1, Jan. 1, 2018, 10 Pages.
"International Search Report and Written Opinion Issued in PCT Application No. PCT/US2019/051613", dated Jun. 9, 2020, 12 Pages.
Grass, et al., "Robust Chemical Preservation of Digital Information on DNA in Silica with Error-Correcting Codes", In Publication of Angewandte Chemie International Edition, vol. 54, Feb. 16, 2015, pp. 2552-2555.
Vanova, et al., "Protocols for dry DNA storage and shipment at room temperature", In Molecular Ecology Resources, vol. 13, Sep. 2013, pp. 890-898.
Lindahl, Tomas, "Instability and Decay of the Primary Structure of DNA", In Nature, vol. 362, Apr. 22, 1993, pp. 709-715.
Nelson, John, "Repair of Damaged DNA for Forensic Analysis", In Final Report Award No. 2006-DN-BX-K018, Jul. 1, 2009, 96 Pages.
Organick, et al., "Random access in large-scale DNA data storage", In Nature Biotechnology, vol. 36, No. 3, Mar. 2018, pp. 242-250.
"Office Action Issued in European Patent Application No. 19779688. 1", dated Apr. 13, 2022, 8 Pages.
"Office Action Issued in European Patent Application No. 19779688. 1", dated Jan. 30, 2023, 6 Pages.

* cited by examiner

*Primary Examiner* — Angela M. Bertagna
*Assistant Examiner* — Carolyn L Greene
(74) *Attorney, Agent, or Firm* — Newport IP, LLC; Benjamin A. Keim (57) ABSTRACT

One or more enzymes are used to repair damage in synthetic DNA molecules that encode digital information. The enzymes are included in a repair mixture containing one or more of DNA polymerase, DNA ligase, T4 Endonuclease, Endonuclease IV, Endonuclease VIII, and uracil glycosylase. The repair mixture may also contain one or more of a buffering solution, oxidized nicotinamide adenine dinucleotide (NAD$^+$), and deoxyribose nucleoside triphosphates (dNTPs). The synthetic DNA molecules are incubated with the repair mixture for approximately four hours. Use of the repair solution allows recovery of the digital information from damaged DNA molecules.

20 Claims, 7 Drawing Sheets

Specification includes a Sequence Listing.

ENZYMATIC DNA REPAIR

SEQUENCE LISTING

The content of the ASCII text file of the sequence listing named "405196-US-NP-MS1-9265US-Sequence-Listing_ST25-as-filed-10-5-18.txt" which is 2 KB in size was created on Oct. 5, 2018 and electronically submitted via EFS-Web is incorporated herein by reference in its entirety.

BACKGROUND

Synthetic deoxyribose nucleic acid (DNA) has use as a storage medium for digital information. DNA can store digital information with greater density and longevity than other storage media. However, DNA is prone to damage from various sources such as ultraviolet (UV) radiation, hydrolysis, thermal disruption, toxins, mutagenic chemicals, and viruses. Damage to the DNA molecules themselves can make it more difficult or impossible to recover the digital information stored in the sequence of nucleotide bases. The storage conditions and length of time in storage can affect the type and extent of damage. For extremely long-term storage, such as thousands of years, DNA is likely to experience damage even under the most protective of storage conditions. For shorter-term storage, the ability to repair errors can make less robust storage options feasible.

Techniques that aid in accurately recovering digital information encoded in damaged DNA can improve the usability of DNA as a storage medium for digital information.

SUMMARY

This disclosure provides techniques for repairing DNA to improve recovery of digital information stored in the sequence of DNA nucleotides. The DNA is repaired by exposure to a repair mixture which contains one or more enzymes such as DNA polymerase, DNA ligase, and endonuclease(s). Enzymatic repair makes more DNA available for sequencing which in turn improves the sequence data from which the stored digital information is retrieved.

Recovering digital information stored in DNA may include amplifying a pool of stored DNA molecules by polymerase chain reaction (PCR) and sequencing the PCR product with a DNA sequencer to generate sequence data. The sequence data, which represents the sequences of nucleotide bases of the individual DNA molecules in the pool, is decoded to regenerate the digital information. If too many of the DNA molecules in the pool are damaged, it may not be possible to obtain sequence data from a sufficient number of the DNA molecules which in turn can make it difficult or impossible to regenerate the digital information. Error correction techniques and storage redundancy can mitigate the effects of some but not all types of damage.

Performing enzymatic repair on damaged DNA can significantly increase the number of individual DNA molecules that are able to be successfully amplified by PCR. Amplification of a greater number of different molecules from the pool of DNA allows for more of the digital information to be reconstructed. In some implementations, the amount of DNA that can be recovered by PCR may be quadrupled following enzymatic repair. This may make the difference between being able to recover all of the digital information or not.

Different enzymes can be used to repair DNA and each enzyme is suited for repairing different types of damage. Examples of enzymes that can function to repair DNA include DNA polymerase, DNA ligase, and endonucleases. Different reaction conditions such as enzyme concentration, temperature, and the length of exposure to a repair mixture also affect repair efficiency. Exposing damaged DNA to the appropriate enzymes under suitable reaction conditions increases the number of distinct DNA molecules from the pool of DNA that are able to be amplified by PCR, and thus, increases the amount of sequence data available to decode and regenerate the digital information.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

DETAILED DESCRIPTION

Polynucleotides such as DNA may be used to store digital information by designing a sequence of nucleotide bases—adenine (A), cytosine (C), guanine (G), and thymine (T)—that encodes the zeros and ones of the digital information. There are various techniques and encoding schemes known to those of skill in the art for using nucleotide bases to represent digital information. See Grass et al., *Robust Chemical Preservation of Digital Information on DNA in Silica with Error-correcting Codes*, 54 Angew. Chem. Int. Ed. 2552 (2015) and Organick et al., *Random access in large-scale DNA data storage*, 36:3 Nat. Biotech. 243 (2018). Advantages of using DNA rather than another storage media for storing digital information include information density and longevity. The DNA repair techniques described in this disclosure can improve the ability to recover sequence information from damaged DNA that would not otherwise be recoverable and to reduce the amount of DNA that must be sequenced in order to be able to regenerate encoded digital information.

The contents of the disclosure may be used with any type of double-stranded (ds) polynucleotide, thus references to "DNA" are illustrative and not intended to limit the application to a particular type of polynucleotide. Use of ribonucleic acid (RNA), DNA-RNA hybrids, nucleotides that include unnatural bases such as dNaM and dTPT3, as well as nucleotides that include fewer than all four natural bases are also included within the scope of the techniques described in this disclosure. Accordingly, "polynucleotide" as used herein may include ds-DNA and ds-RNA with both natural bases and/or unnatural bases. DNA as used herein also includes DNA strands that have unnatural bases and/or include fewer than all of the natural bases.

Figure 1:
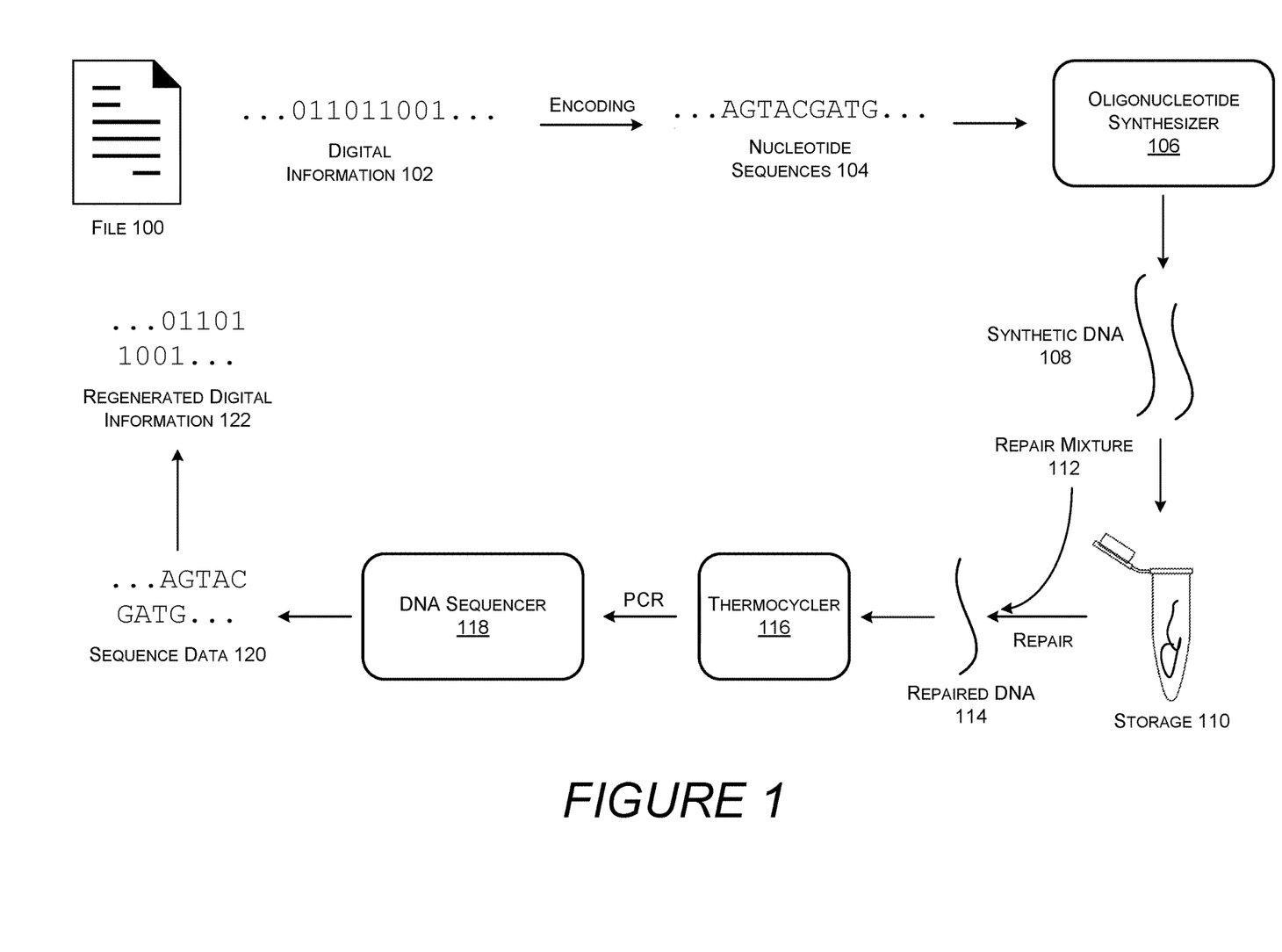
FIG. 1 is a diagram illustrating equipment and techniques that may be used for encoding digital information from a computer file in DNA and then later regenerating that digital information.

FIG. 1 illustrates a schematic representation of using DNA to store digital information and regenerating the digital information from the DNA. A computer file 100 represents any type of file or document that may be accessed by a conventional computer. For example, the file 100 may be a video file or a word-processing document. The file 100 is one example of digital information 102. However, digital information 102 can also include other types of binary sequences such as sequences that do not encode a computer file 100.

The digital information 102 may be converted to a string of nucleotide bases. The number of nucleotide bases needed to encode the entirety of the digital information 102 may exceed the length of a single synthetic DNA molecule. Thus, nucleotide encoding of the digital information 102 is split into multiple nucleotide sequences 104. There may be hundreds, thousands, or millions of nucleotide sequences 104 needed to represent a single file 100. At this stage, the nucleotide sequences 104 are not DNA molecules only strings out of nucleotide bases (e.g., a sequence of letters approximately 80-150 characters long) that, when recombined and properly decoded, produces the digital information 102. These strings of letters provide instructions for making a pool of DNA molecules that collectively will store the digital information 102. The nucleotide sequences 104 may include subsequences that serve purposes other than encoding digital information 102 such as, for example, identification of the file 100 and identification of how each of the individual nucleotide sequences 104 should be recombined with each other.

Once the nucleotide sequences 104 are designed, each of these nucleotides strings are provided to an oligonucleotide synthesizer 106 that creates a pool of synthetic DNA 108 with the specified sequences. The oligonucleotide synthesizer 106 performs chemical synthesis of polynucleotides by joining nucleosides in the sequences specified by the nucleotide sequences 104. With current polynucleotide synthesis technology, the chain grows in the 3' to 5' direction, which is backwards relative to natural biosynthesis. Being a chemical process, it is possible for incorrect interactions to occur leading to defective products. The longer the polynucleotide sequence that is being synthesized, the more defects there are, thus with current technology this process is only practical for producing relatively short sequences of nucleotides. The current practical limit is about 100-200 base pairs (bp) for a DNA molecule with sufficient quality. Accordingly, the digital information 102 is divided into multiple nucleotide sequences 104 each with a length within the range of about 100 to 200 bp. Each one of the nucleotide sequences 104 may be synthesized multiple times by the oligonucleotide synthesizer 106 to create multiple synthetic DNA molecules each having the same sequence.

The synthetic DNA 108 produced by the oligonucleotide synthesizer 106 is a collection of individual DNA molecules that have the sequences indicated by the nucleotide sequences 104 (including any errors that may be introduced by the synthesis process) and taken together encode the digital information 102. In the pool of synthetic DNA 108, there may be redundancy in that multiple molecules having the same sequence as well as variety because a plurality of different nucleotide sequences 104 are included.

The synthetic DNA 108 may be placed into storage 110 until there is a need to retrieve the file 100. The storage 110 may be short-term storage such as in a buffered aqueous solution. The storage 110 may be long-term storage such as archival storage in which the synthetic DNA 108 is kept for tens, hundreds, or even thousands of years in a dried or otherwise preserved state. Regardless of the storage technique, the synthetic DNA 108 may suffer damage while in storage 110.

There are many types of damage that can occur to DNA such as hydrolytic damage, oxidative damage, radiation damage, and chemical damage. Hydrolytic DNA damage involves deamination or the total removal of individual bases. AP (apurinic/apyrimidinic) sites are chemically weak and are prone to single strand-break. Hydrolytic damage may result from the biochemical reactions of various metabolites as well as the overabundance of reactive oxygen species. Oxidative DNA damage refers to the oxidation of specific bases. 8-hydroxydeoxyguanosine (8-OHdG) is the most common marker for oxidative DNA damage. 8-OHdG is formed and enhanced most often by chemical carcinogens. Ultraviolet and other types of radiation can damage DNA in the form of DNA strand breaks. This involves a cut in one or both DNA strands. Ultraviolet-induced damage can also result in the production of pyrimidine dimers, where covalent cross-links occur in cytosine and thymine residues. The most common pyrimidine dimers are cyclobutane pyrimidine dimers (CPD) and pyrimidine (6-4) pyrimidone photoproducts (6-4PP). Chemical DNA damage may result from exposure to polycyclic aromatic hydrocarbons (PAHs). PAHs are potent, ubiquitous atmospheric pollutants commonly associated with oil, coal, cigarette smoke, and automobile exhaust fumes. A common marker for DNA damage due to PAHs is Benzo(a)pyrene diol epoxide (BPDE). BPDE is found to be very reactive and known to bind covalently to proteins, lipids, and guanine residues of DNA to produce BPDE adducts. Damaged DNA may be present in storage 110 and the types and extent of damage may prevent analysis of the DNA which in turn prevents recovery of the digital information 102.

Double-strand breaks are difficult to repair because the two portions of the DNA strand may become separated from each other and unable to be rejoined. Single-strand breaks are easier to repair because the backbone of a complementary stand keeps the two strands annealed to each other and retains the overall structure of the DNA strand. The techniques included in this disclosure are useful if the damage results in singularly damaged bases (e.g. 8-OHdG) or single strand breaks.

DNA molecules taken from storage 110 may be repaired with a repair mixture 112 that contains one or more enzymes. The enzymes included in the repair mixture 112 may be polymerases, ligases, endonucleases, and/or glycosylases. DNA polymerases are enzymes that synthesize DNA molecules from deoxyribonucleotides, the building blocks of DNA. DNA polymerases add nucleotides to the 3'-end of a DNA strand, one nucleotide at a time. DNA ligase is a specific type of enzyme, a ligase, that facilitates the joining of DNA strands together by catalyzing the formation of a phosphodiester bond. A ligase is an enzyme that can catalyze the joining of two large molecules by forming a new chemical bond. Endonucleases are enzymes that cleave the phosphodiester bond within a polynucleotide chain. Endonucleases play a role in DNA repair. AP endonucleases, specifically, catalyze the incision of DNA exclusively at AP sites and therefore prepare DNA for subsequent excision, repair synthesis, and ligation. Glycosylases are enzymes that hydrolyze glycosyl compounds. DNA glycosylases are a family of enzymes involved in base excision repair. Base excision repair is the mechanism by which damaged bases in DNA are removed and replaced. DNA glycosylases catalyze the first step of this process. Glycosylases remove the damaged nitrogenous base while leaving the sugar-phosphate backbone intact, creating an AP site.

The DNA removed from storage 110 may be incubated with the repair mixture 112 under any number of different conditions. For example, the DNA from storage 110 may be combined with the repair mixture 112 at 37° C. for a number of hours such as two, three, four, five, or six hours.

After contacting the DNA from storage 110 with the repair mixture 112, repaired DNA 114 may be placed into a thermocycler 116 and amplified by PCR. PCR is a well-known technique used in molecular biology to exponentially amplify a single copy or a few copies of a specific segment of DNA to generate thousands to millions of copies of that particular DNA segment. Many PCR methods rely on thermal cycling. Thermal cycling exposes reactants to cycles of repeated heating and cooling to permit different temperature-dependent reactions—specifically, DNA melting and enzyme-driven DNA replication. PCR employs two main reagents: primers (which are short single strand DNA fragments known as oligonucleotides that are a complementary sequence to the target DNA region) and a DNA polymerase. In the first step of PCR, the two strands of the DNA double helix are physically separated at a high temperature in a process called DNA melting. In the second step, the temperature is lowered and the primers bind to the complementary sequences of DNA. The two DNA strands then become templates for DNA polymerase to enzymatically assemble a new DNA strand from free nucleotides, the A, C, G, and T of DNA. As PCR progresses, the DNA generated is itself used as a template for replication, setting in motion a chain reaction in which the original DNA template is exponentially amplified. The thermocycler 116 is a machine commonly used to amplify segments of DNA via PCR. The design of most thermocyclers 116 includes a thermal block with holes where tubes holding reaction mixtures can be inserted. The thermocycler 116 then raises and lowers the temperature of the block in discrete, pre-programmed steps to provide the thermal cycling.

PCR amplification increases the number of DNA strands that are available for analysis by a DNA sequencer 118. PCR, however, may introduce errors so it is possible that the DNA molecules produced by PCR are not all identical copies of the repaired DNA 114. Use of the thermocycler 116 and amplification of the repaired DNA 114 through PCR is not required for all types of DNA sequencing. Thus, the techniques provided in this disclosure are equally applicable for implementations that do not use PCR as a pre-sequencing step.

The DNA sequencer 118 detects the sequence of individual nucleotides in a sample of DNA and generates sequence data 120 representing the sequence. Given a sample of DNA, such as a PCR product, a DNA sequencer 118 determines the order of the nucleotide bases. This is then reported as the sequence data 120 which may be a text string that is called a "read." The read may be in any suitable format such as plain text, FASTQ, EMBL, or FASTA. There are many different types of DNA sequencers 118 and sequencing technology. The contents of this disclosure may be used with any method or technology that can determine the order of the nucleotide bases in a strand of DNA.

A sequencing technology that can be used is sequencing-by-synthesis (Illumina® sequencing). Sequencing by synthesis is based on amplification of DNA on a solid surface using fold-back PCR and anchored primers. Adapters are added to the 5'- and 3'-ends of the fragments. DNA fragments that are attached to the surface of flow cell channels are extended and bridge amplified. The fragments become double-stranded, and the double-stranded molecules are denatured. Multiple cycles of solid-phase amplification followed by denaturation can create several million clusters of approximately 1,000 copies of single-stranded DNA molecules of the same template in each channel of the flow cell. Primers, DNA polymerase, and four fluorophore-labeled, reversibly terminating nucleotides are used to perform sequential sequencing. After nucleotide incorporation, a laser is used to excite the fluorophores, an image is captured, and the identity of the first base is recorded. The 3' terminators and fluorophores from each incorporated base are removed and the incorporation, detection, and identification steps are repeated. Sequencing-by-synthesis has a relatively low error rate (e.g., less than 1%) and produces read lengths of a few hundred base pairs. This length is generally sufficient to read the entire length of a single synthetic polynucleotide.

Another sequencing technique that can be used is nanopore sequencing. A nanopore is a small hole of the order of one nanometer in diameter. Immersion of a nanopore in a conducting fluid and application of a potential across the nanopore results in a slight electrical current due to conduction of ions through the nanopore. The amount of current that flows through the nanopore is sensitive to the size of the nanopore. As a polynucleotide molecule passes through a nanopore, each nucleotide on the polynucleotide molecule obstructs the nanopore to a different degree. Thus, the change in the current passing through the nanopore as the polynucleotide molecule passes through the nanopore represents a reading of the polynucleotide sequence. Nanopore sequencing has much higher error rates (e.g., over 10%) than sequencing-by-synthesis. However, the read lengths of Nanopore sequencing are much longer—up to 800,000 bp long.

The sequence data 120 output by the DNA sequencer 118 may be decoded to create regenerated digital information 122. Decoding of the sequence data 120 may be the reverse of the process used for encoding nucleotide sequence 104. This encoding/decoding process may include error correction and redundancy so that the digital information 102 is correctly regenerated even if there are errors introduced such as by the oligonucleotide synthesizer 106, damage while in storage, PCR amplification, or the DNA sequencer 118. Errors introduced by the oligonucleotide synthesis, PCR amplification, and DNA sequencing are generally of a type and scope that can be addressed by error correction and redundancy. In the context of digital information recovery, damage to the synthetic DNA 108 must be considered in terms of the pool of individual DNA molecules. Damage to a single DNA molecule may have no effect on the ultimate ability to create the regenerated digital information 122 if the sequence data 120 encoded by that damaged DNA molecule is able to be obtained from other DNA molecules in the pool. However, extensive damage during storage 110 to a large number of the individual DNA molecules in the pool of synthetic DNA 108 may result in the recovered digital information 122 being inaccurate or may even prevent recovery of the original digital information 102. Thus, in some instances, enzymatic repair of the synthetic DNA 108 prior to sequencing may be necessary to obtain a sufficiently representative sample of the synthetic DNA 108 to recover the stored digital information 102.

ILLUSTRATIVE PROCESSES

Figure 2:
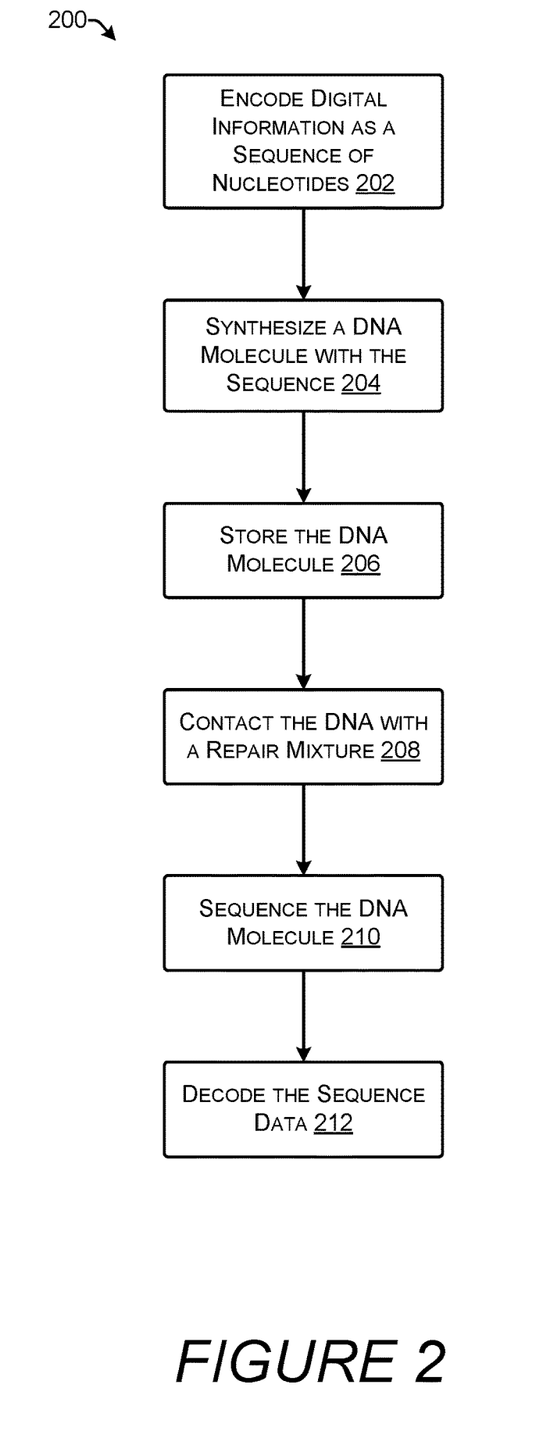
FIG. 2 is a flow diagram showing an illustrative process for encoding digital information in DNA, storing the DNA, and then decoding the sequence data from the DNA to recover the digital information.
Figure 3:
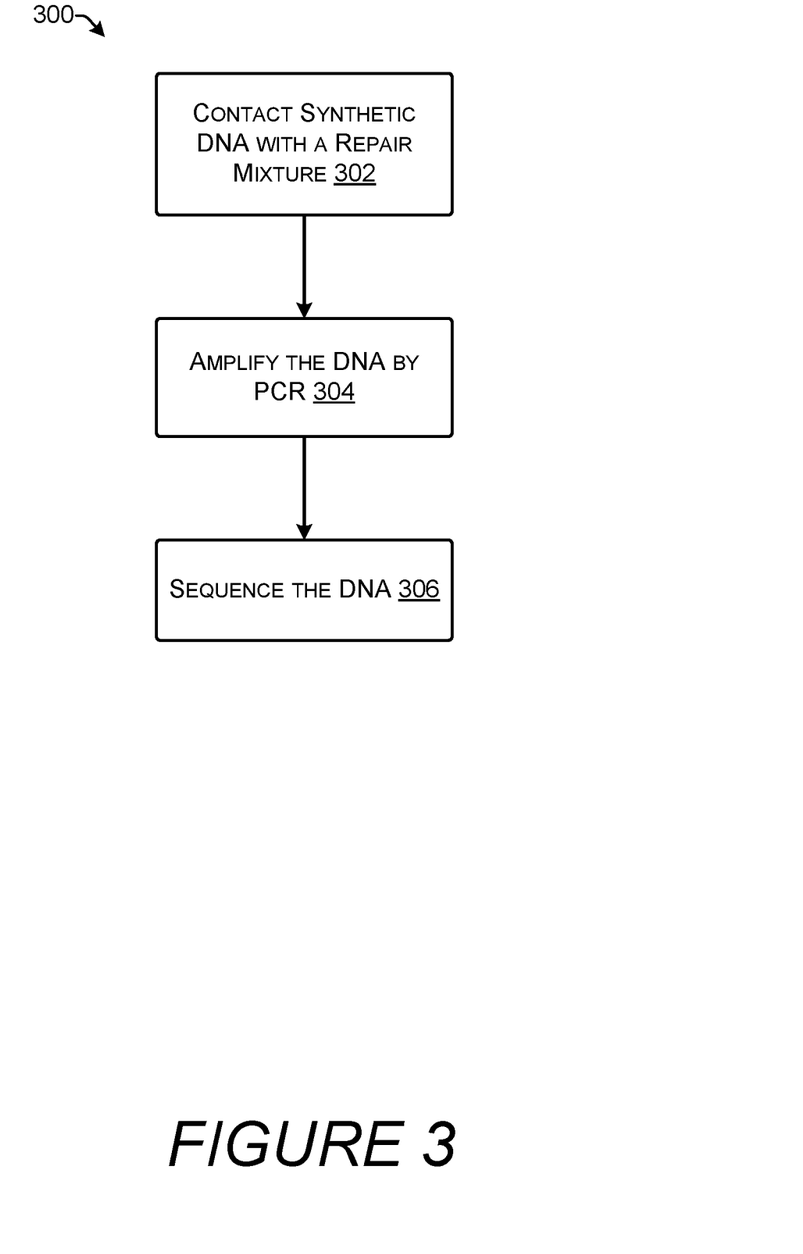
FIG. 3 is a flow diagram showing an illustrative process for repairing synthetic DNA prior to amplification by PCR and sequencing.
Figure 4:
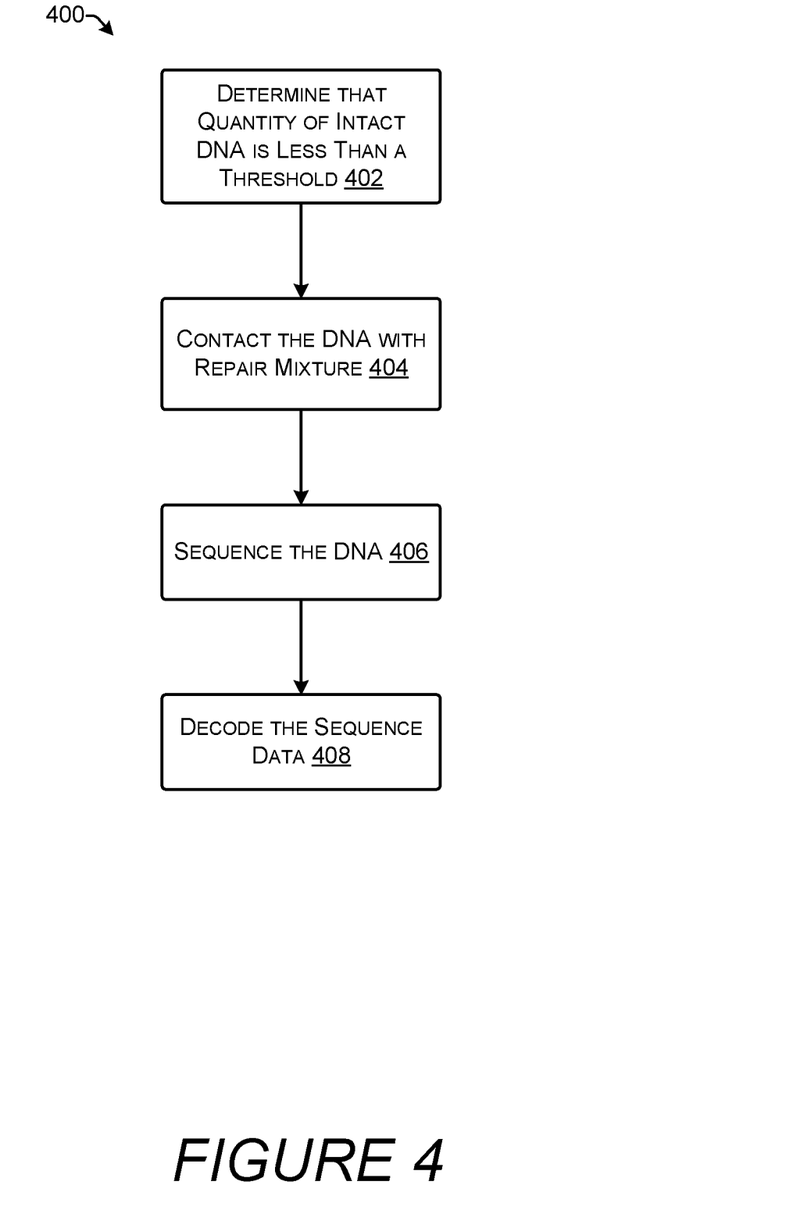
FIG. 4 is a flow diagram showing an illustrative process for contacting DNA with a repair mixture if there is less than a threshold quantity of intact DNA.

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process or an alternate process. Moreover, it is also possible that one or more of the provided operations is modified or omitted. FIGS. 2-4 may be implemented in whole or part by the system and equipment shown in FIG. 1.

FIG. 2 shows a process 200 for repairing stored DNA that encodes digital information.

At 202, digital information is encoded as a sequence of nucleotides. The digital information may represent all or a portion of a computer file or executable computer program. Encoding may use any encoding technique known to those of skill in the art for translating binary information into a code comprising nucleotide bases. The encoding schema may include error correction such as, for example, Hamming codes, Reed-Solomon codes, multidimensional parity, Bose-Chaudhuri-Hocquenghem codes, or any other suitable error-correction code At 204, a synthetic DNA molecule is synthesized. The synthetic DNA molecule includes at least part of the sequence of nucleotides that encodes the digital information. The synthetic DNA molecule may also include nucleotides encode other information. The synthetic DNA molecule may be synthesized by an oligonucleotide synthesizer such as the oligonucleotide synthesizer 106 introduced in FIG. 1. The length of the synthetic DNA molecule may be between about 80-250 bp, between about 100-180 bp, or between about 120-160 bp.

At 206, the synthetic DNA molecule is stored. The synthetic DNA molecule may be stored using any technique for storing DNA. For example, the synthetic DNA molecule may be stored in a buffered aqueous solution (e.g., Tris-EDTA) and refrigerated at approximately 4° C. Additionally, the synthetic DNA molecule may be frozen at −20° C. or stored as a precipitate in ethanol at −80° C. DNA may also be stored in liquid nitrogen at −196° C. The synthetic DNA molecule may be stored at room temperature such as by drying the DNA and storing it on a paper card (e.g., a Whatman® FTA® card) or another substrate.

At 208, the synthetic DNA molecule is contacted with a repair mixture. The repair mixture may be the repair mixture 112 introduced in FIG. 1. The repair mixture includes at least one enzyme and may include any or all of DNA polymerase, DNA ligase, or an endonuclease. For all the enzymes described in this disclosure, either enzymes derived from natural sources or enzymes obtained from recombinant sources may be used.

One suitable DNA polymerase that may be used is Bst DNA polymerase. Bst polymerase is derived from *Bacillus stearothermophilus* a rod-shaped, Gram-positive bacterium. Bst polymerase has a helicase-like activity, making it able to unwind DNA strands.

One suitable DNA ligase that may be used is Taq DNA ligase. Taq DNA Ligase is a thermostable ligase that catalyzes the formation of a phosphodiester bond between the 5'-phosphate and the 3'-hydroxyl of two adjacent DNA strands. This enzyme is derived from the thermophilic bacteria Therms aquaticus.

One suitable endonuclease that may be included in the repair mixture is T4 Endonuclease V originally isolated from Enterobacteria phage T4. This enzyme has both DNA glycosylase and APlyase activity. T4 Endonuclease V recognizes cis-syn-cyclobutane pyrimidine dimers caused by UV irradiation. The enzyme cleaves the glycosyl bond of the 5'-end of the pyrimidine dimer and the endonucleolytic activity cleaves the phosphodiester bond at the AP site.

One suitable endonuclease that may be used for DNA repair is Endonuclease IV. Endonuclease IV can act on a variety of oxidative damage in DNA. The enzyme is an apurinic/apyrimidinic (AP) endonuclease that will hydrolyze intact AP sites in DNA. AP sites are cleaved at the first phosphodiester bond that is 5' to the lesion leaving a hydroxyl group at the 3' terminus and a deoxyribose 5'-phosphate at the 5'-terminus. The enzyme also has a 3'-diesterease activity and can release phosphoglyceraldehyde, intact deoxyribose 5-phosphate and phosphate from the 3'-end of DNA.

Another suitable endonuclease that may be included in the repair mixture is Endonuclease VIII. This endonuclease is from *E. coli* acts as both an N-glycosylase and an AP-lyase. The N-glycosylase activity releases damaged pyrimidines from double-stranded DNA, generating an apurinic (AP site). The AP-lyase activity cleaves 3' and 5' to the AP site leaving a 5'-phosphate and a 3'-phosphate. Damaged bases recognized and removed by Endonuclease VIII include urea, 5, 6-dihydroxythymine, thymine glycol, 5-hydroxy-5-methylhydantoin, uracil glycol, 6-hydroxy-5,6-dihydrothymine and methyltartronylurea (1, 2). While Endonuclease VIII is similar to Endonuclease III, Endonuclease VIII has β and δ lyase activity while Endonuclease III has only β lyase activity.

Contacting the synthetic DNA molecule with repair mixture may be performed under a variety of reaction conditions. The synthetic DNA molecule may be incubated with the reaction mixture at a temperature of 20-60° C., 30-50° C., 35-45° C., or about 37° C. The length of the incubation may be 2-8 hours, 3-5 hours, or about four hours. Notably, prior to contacting that synthetic DNA with repair mixture, the synthetic DNA may be maintained at a temperature of around room temperature or cooler. Thus, the previous steps of process 200 may be performed at temperatures of less than 25° C., less than 22° C., less than 19° C., less than 16° C., or cooler. As used herein, "approximately" or "about" denotes a range of ±10% of the stated value.

At 210, following contact with the repair mixture, the synthetic DNA is sequenced to generate sequence data. Sequencing may be performed by any suitable technique for DNA sequencing. For example, sequencing may be performed by the DNA sequencer 118 introduced in FIG. 1.

At 212, the sequence data obtained at 210 is decoded to obtain regenerated digital information. If the synthetic DNA has been sufficiently repaired, and any other errors introduced in the process have been mitigated, then the regenerated digital information will contain the same or nearly the same binary sequence as the digital information that was originally encoded in the nucleotides.

FIG. 3 shows a process 300 for pre-sequencing processing of DNA that includes enzymatic repair.

At 302, synthetic DNA is contacted with a repair mixture. The repair mixture may be the repair mixture 112 introduced in FIG. 1. The repair mixture contains one or more enzymes suitable for repairing DNA. In an implementation, the repair mixture includes at least one of Bst DNA polymerase, Taq DNA ligase, Endonuclease IV, T4 Endonuclease V, or Endonuclease VIII. In an implementation, the repair mixture includes Bst DNA polymerase, Taq DNA ligase, Endonuclease IV, T4 Endonuclease V, and Endonuclease VIII. The repair mixture may also be formulated so that it includes only a single enzyme. For example, the repair mixture may contain only the enzyme T4 Endonuclease V or Endonuclease IV. The repair mixture formulated with a single enzyme may contain other non-enzymatic components such as water, buffers, dNTPs, and oxidized nicotinamide adenine dinucleotide ($NAD^+$).

The synthetic DNA may be DNA that is synthesized by an oligonucleotide synthesizer such as the oligonucleotide synthesizer 106. The synthetic DNA has a sequence that is predetermined at least in part by the encoding of the digital information. A length of the synthetic DNA may be between approximately 50-200 bp, 80-180 bp, or 120-160 bp. Contacting the synthetic DNA with the repair mixture may be performed at a temperature of about 37° C. for about four hours.

At 304, the synthetic DNA is amplified by PCR. PCR may be performed by use of a thermocycler such as the thermocycler 116 introduced in FIG. 1. Repairing the synthetic DNA through contact with repair mixture increases the number of intact strands of DNA that are able to be amplified by the primers used for PCR. This results in amplification of an increased number of different DNA strands from the pool of DNA as compared to amplifying the synthetic DNA without use of the repair mixture. Thus, the amplification product following repair provides a better representation of the variety of DNA sequences stored in the pool of DNA. The increase in number of different DNA strands amplified as a result of preparing the DNA with the repair mixture, as compared to PCR amplification of the synthetic DNA under the same conditions without repair, may be an increase of approximately 1.5 times, 1.8 times, 2.0 times, 4.0 times, or more. Thus, in some implementations contacting the synthetic DNA with the repair mixture at 302 may double the amount of DNA produced by PCR at 304.

At 306, the synthetic DNA following PCR amplification is sequenced. The sequencing may be performed by any suitable technique for reading the nucleotide sequence of a DNA molecule such as the DNA sequencer 118 introduced in FIG. 1. The increase in number of intact DNA strands as a result of using the repair mixture provides more DNA different molecules to be sequenced. The greater number of different DNA molecules allows sequencing to capture more of the variety of DNA stored in the DNA pool sequences and may allow the sequence data digital information to be decoded with less stringent sequencing conditions. One way in which the sequencing conditions may be relaxed is by decreasing the coverage or read depth. Coverage (or depth) in DNA sequencing is the number of unique reads that include a given nucleotide in the reconstructed sequence.

FIG. 4 shows a process 400 for recovering digital information from damaged DNA strands. The goal of recovering digital information from DNA used for data storage is to be able to reconstruct the original digital information without error. This is illustrated in FIG. 1 by the sequence of the regenerated digital information 122 being the same as the digital information 102. Damage caused to the DNA strands during storage may be thought of as "noise" in a communication channel DNA repair is a technique for reducing the noise.

At 402, it is determined that the quantity of intact DNA strands in a sample of synthetic DNA is less than a threshold level. The quantity of intact strands of DNA in a sample may be measured by quantitative PCR (qPCR). qPCR uses the linearity of DNA amplification to determine the quantity of DNA in a sample. By using a fluorescent reporter in the reaction, it is possible to measure DNA generation in the qPCR assay as the PCR reaction proceeds in real time. The number of PCR cycles at which the fluorescence exceeds a detection threshold (e.g., 0.2 fluorescent units) and becomes measurable is called the quantification cycle (Cq). Starting samples that include a larger amount of amplifiable DNA (i.e., intact DNA strands with primer binding sites) reach this threshold with fewer PCR cycles than samples with a smaller amount of DNA. For sequences with an optimal PCR efficiency (100%), each PCR cycle doubles the quantity of DNA, so an increase in the Cq value of 1 is equivalent to detecting a 50% loss of the initial quantity of DNA. Thus, Cq values are inversely proportional to the amount of target DNA in the sample.

The threshold level may be based on a quantity of DNA needed to successfully recover the digital information. The quantity of DNA does not directly correlate to the ability to recover digital information. A large number of only a few different DNA strands may provide a reasonable volume of DNA, but the sequences encoded by the DNA strands will not include all of the data necessary to regenerate the digital information. However, assuming that damage caused during storage is distributed roughly randomly across the pool of DNA molecules calculations may be made to identify the volume of DNA that is likely to contain a sufficient diversity of individual DNA molecules.

The threshold level may also be based on a change in Cq values for the synthetic DNA before and after storage. After synthesis of the synthetic DNA, the aliquot of the pool may be taken and the quantity of DNA measured using qPCR. This provides a starting value for the amount of DNA prior to storage. After storage, the Cq value is measured again. As discussed above, a decrease in the Cq value of one indicates roughly a halving of the available DNA. If the difference in Cq values is more than a threshold number (e.g., 1.0, 2.0, 3.0). The threshold number may be determined experimentally based on experiments recovering digital information from other pools of DNA. The technique for encoding the digital information in the synthetic DNA and the level of redundancy in the synthesis of synthetic DNA molecules may affect the threshold value.

At 404, the synthetic DNA is contacted with repair mixture. The repair mixture includes at least one of a DNA polymerase, a DNA ligase, or an endonuclease. The repair mixture may be the same as the repair mixture 112 introduced in FIG. 1. Alternatively, if it is determined that there is a sufficient quantity of intact DNA strands to proceed, the synthetic DNA may be sequenced without first using a repair mixture.

At 406, the synthetic DNA is sequenced to generate sequence data. The synthetic DNA may be sequenced by the DNA sequencer 118 introduced in FIG. 1. Depending on the quantity of DNA and the sequencing technique used, sequencing may be preceded by PCR amplification of the repaired DNA.

At 408, the sequence data is decoded to obtain regenerated digital information.

EXAMPLES

Figure 5:
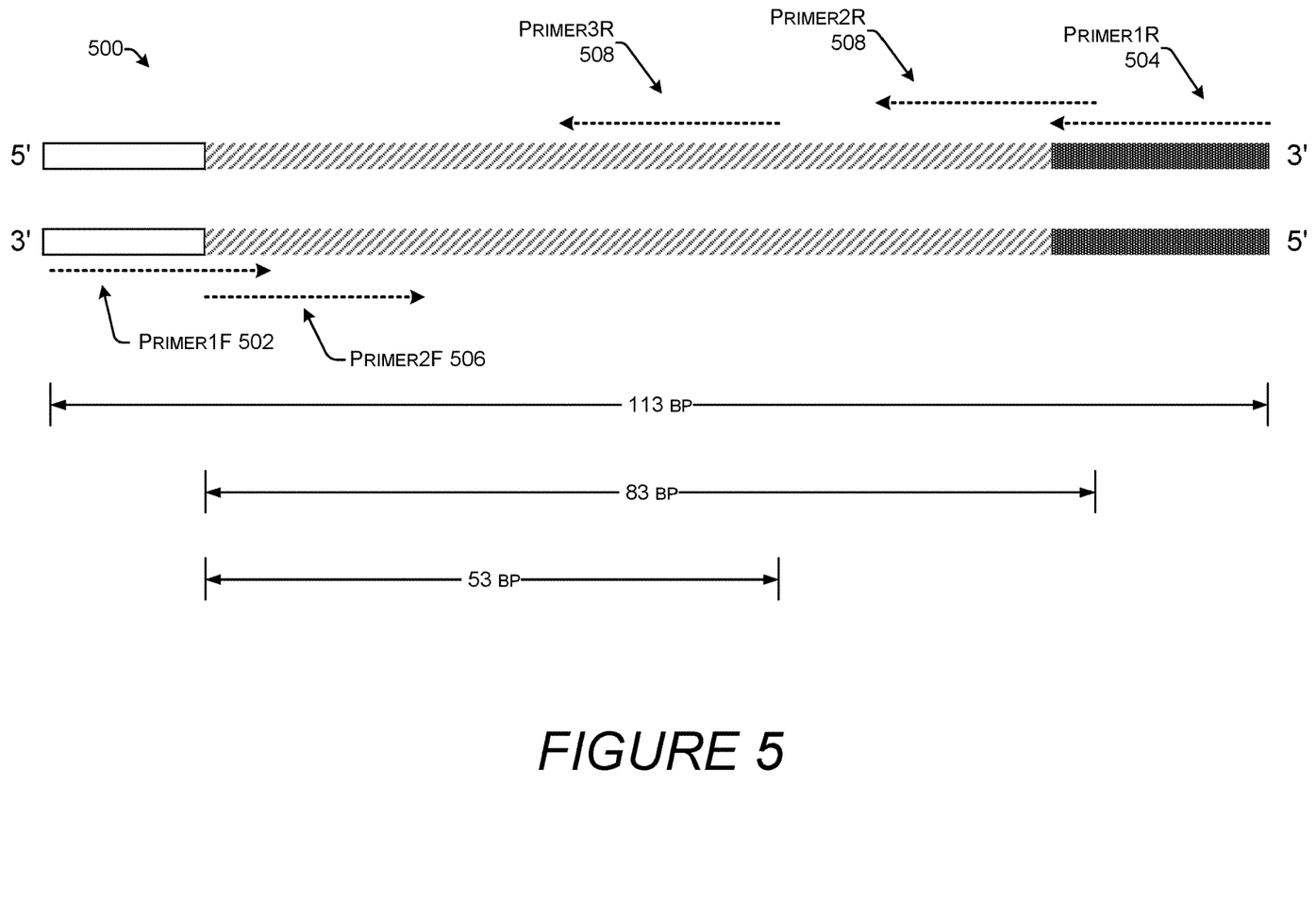
FIG. 5 is a diagram showing a schematic representation of a single double-stranded DNA molecule that includes five separate primer locations used to generate amplification products of three different lengths.

FIG. 5 shows a schematic diagram of a synthetic dsDNA strand 500 and five different primer that bind to the DNA strand 500. The DNA strand 500 has a length of 113 bp (SEQ ID: 1). This DNA strand 500 is used in the following examples.

The first forward primer, Primer1F 502 (SEQ ID: 2), binds to the end of the DNA strand 500. When paired with the first reverse primer, Primer1R 504 (SEQ ID: 3) which binds to the other end of the DNA strand 500, the amplification product is the entire 113 bp length of the DNA strand 500. A second forward primer, Primer2F 506 (SEQ ID: 4), binds to the DNA strand 500 partially overlapping with the binding site of the Primer1F 502. The PCR amplification product using Primer2F 506 as the forward primer and a second reverse primer, Primer2R 508 (SEQ ID: 5) for as the reverse primer is an 83 bp long fragment from the middle of the DNA strand 500. A third primer, Primer3R 508 (SEQ ID: 6), located near the middle of the DNA strand 500 when used together with the second forward primer, Primer2F 506, creates an amplification product that is 53 bp long.

These three different lengths of sequences that can be created from the DNA strand 500 are used to test the effect of strand length on DNA repair and recovery.

Effects of Strand Length and Enzymatic Repair on DNA Recovery

Figure 6:
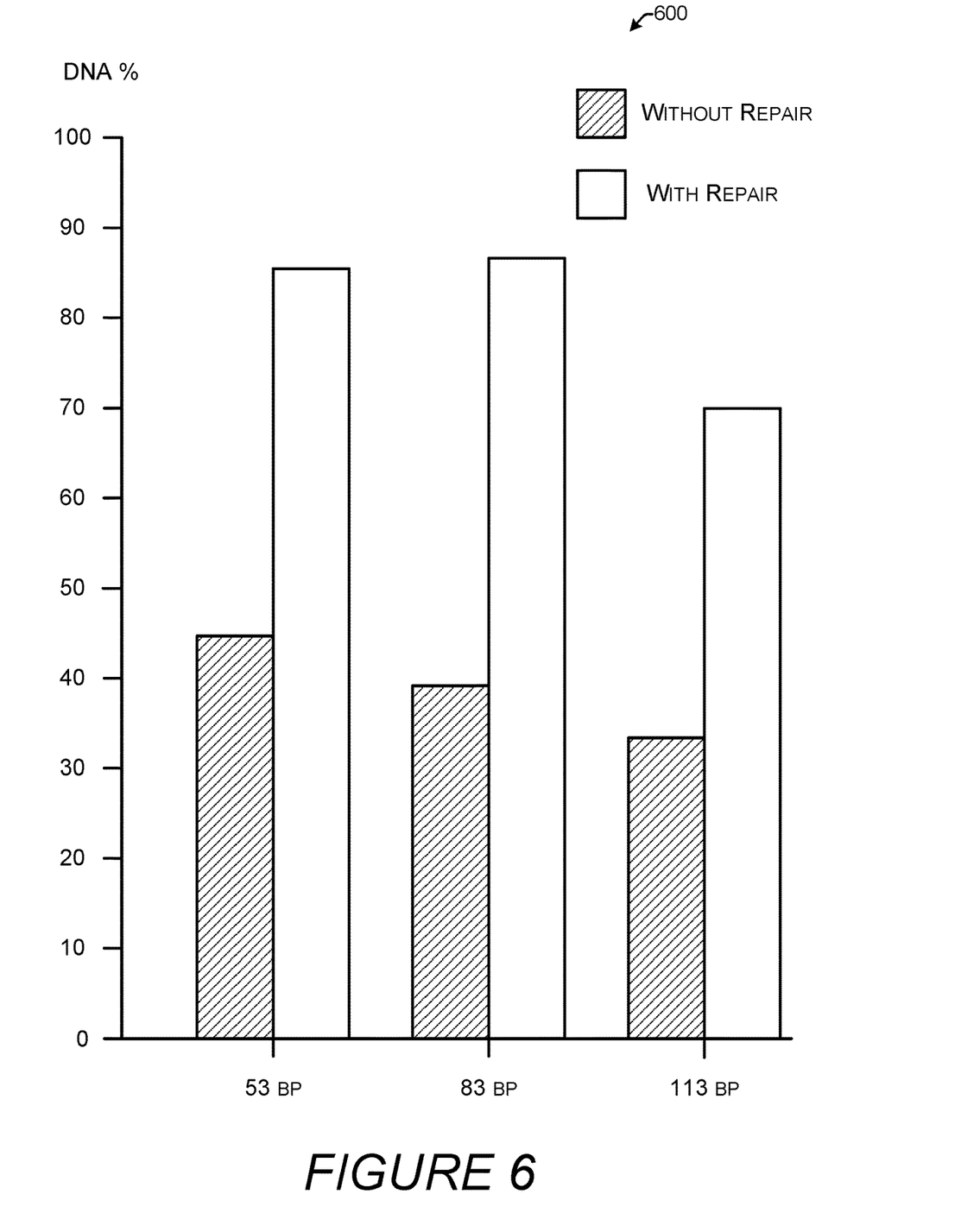
FIG. 6 is a bar chart showing that enzymatic repair of DNA molecules doubles the amount of DNA as compared to DNA stored under the same conditions without enzymatic repair.

FIG. 6 shows a bar chart 600 comparing the amount of intact DNA in samples with and without enzymatic repair. DNA samples of three different lengths, 53 bp, 83 bp, and 113 bp were created from the DNA strand 500 of FIG. 5 using the primers described above. The DNA samples were exposed to high heat and high humidity to simulate aging. In this example, the DNA samples were stored in an oven at 70° C. and 50% relative humidity (RH) for two hours. This simulates approximately 15 years of storage at room temperature and 20% RH. Exposure to the high heat and moisture is believed to cause primarily hydrolytic damage to the DNA samples. Without being bound by theory, it is believed that damage to the DNA samples includes breaks in the backbones of the DNA strands.

The initial concentration of the DNA samples, shown on the vertical axis of the bar chart 600 as 100%, was determined by measuring DNA concentration for each sample prior to exposure to the high heat and humidity. In this example, quantitative PCR (qPCR) was used to measure the amount of DNA in the samples both before and after exposure to the high heat and high humidity. The qPCR was performed using a Roche LightCycler® 96 real-time PCR cycler.

Without enzymatic repair, over half of the available DNA was lost during the exposure to high heat and high humidity. The percent of DNA lost increased with the length of the DNA sample. For the 53 bp DNA strand, about 55% of the original DNA was lost and for the 113 bp DNA strand, about 65% of the original DNA was lost.

However, with enzymatic repair, the amount of intact DNA that could be recovered was approximately double the recovery from the unrepaired samples. For both the 53 bp DNA strand and the 83 bp DNA strand, approximately 85% of the original DNA quantity was recovered following enzymatic repair with a repair mixture. For the longer, 113 bp DNA sample over 70% of the original DNA quantity was recovered.

In this example, the repair mixture was PreCR® Repair Mix available from New England BioLabs, Inc. (catalog # M0309S). PreCR® Repair Mix includes Taq DNA Ligase, Endonuclease IV, Bst DNA Polymerase, formamidopyrimidine DNA glycosylase (Fpg), Uracil-DNA Glycosylase (UDG), T4 PDG (T4 Endonuclease V) and Endonuclease VIII. After exposure to the high temperature and humidity, the DNA samples were incubated with the PreCR® Repair Mix, dNTPs, NAD$^+$, in a buffered solution at 37° C. for four hours with shaking. The contents of the PreCR® Repair Mix are known but the concentrations of the enzymes are not.

Comparison of Incubation Times

Figure 7:
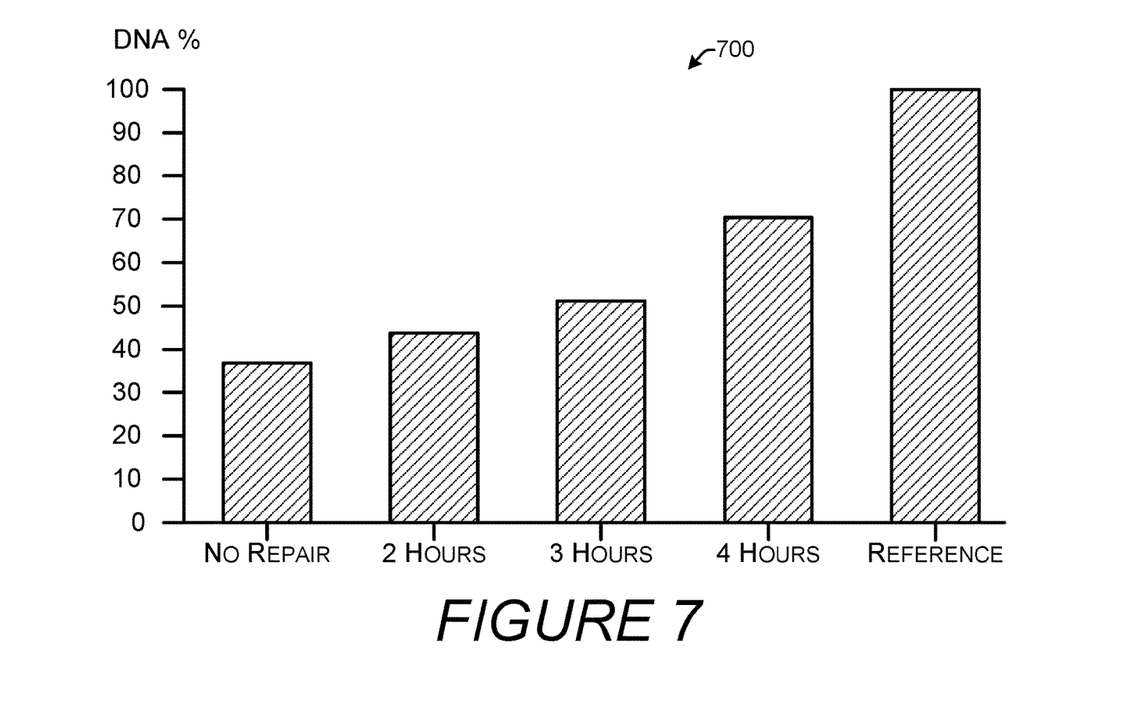
FIG. 7 is a bar chart showing that four hours of incubation with a repair mixture yields a higher concentration of DNA than shorter incubation times.
Figure 8:
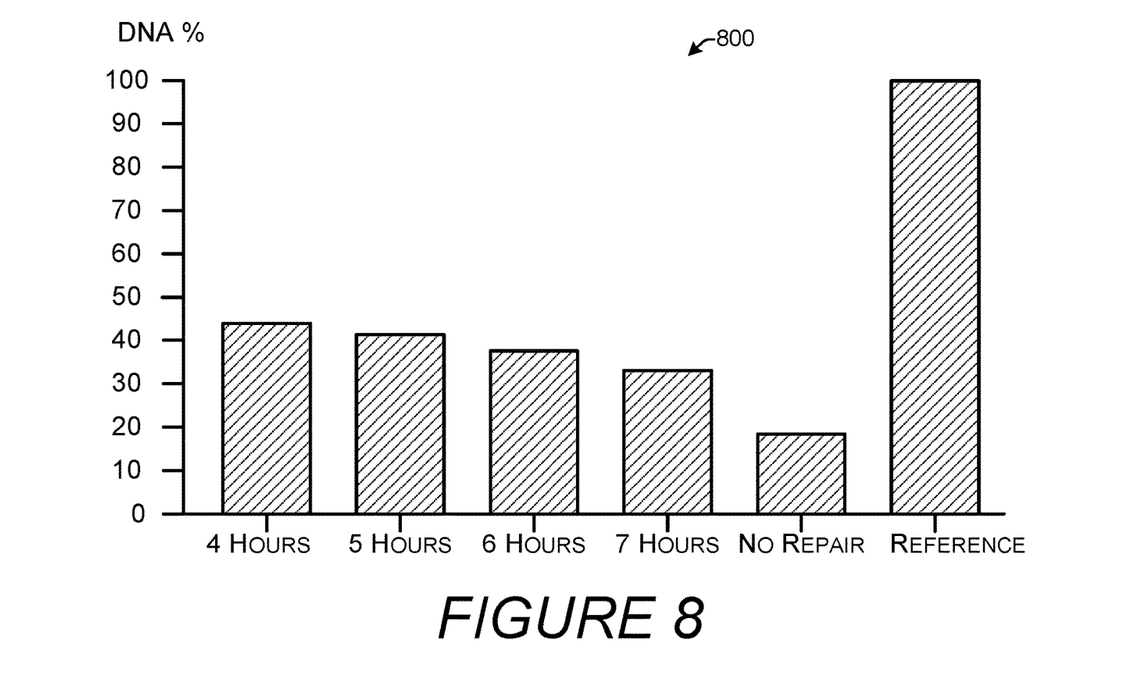
FIG. 8 is a bar chart showing that four hours of incubation with a repair mixture yields a higher concentration of DNA than longer incubation times.

FIGS. 7 and 8 are bar charts 700 and 800 showing the effect of repair time on the amount of DNA recovered from damaged DNA samples. The samples analyzed in FIGS. 7 and 8 are the full-length 113 bp DNA strand 500 introduced in FIG. 5. The repaired samples were incubated with PreCR® Repair Mix under the conditions described above. DNA quantities were measured by qPCR using a Roche LightCycler® 96.

The samples shown in the bar chart 700 of FIG. 7 were exposed to 70° C. temperature and 50% RH for three hours. The column labeled "Reference" represents the quantity of DNA in the samples prior to exposure to high heat and high humidity. Without repair, less than 40% of the original quantity of DNA was recovered. The amount of DNA recovered increased progressively as the length of incubation with the repair mixture increased. The highest recovery of approximately 70% was obtained after incubation with the repair mixture for four hours.

The sample values shown in bar chart 800 of FIG. 8, were generated under the same conditions used to generate the data shown in FIG. 7 except that the length of exposure to 70° C. temperature and 50% RH was four hours After this length of exposure to high heat and high humidity, only about 20% of the unrepaired DNA sample remained. Interestingly, increasing the length of incubation with the repair mixture above four hours decreased the amount of DNA recovery. In this set of samples, the highest amount of DNA recovery which was approximately 45% of the original amount, was obtained after incubation with the repair mixture for four hours. The difference in the amount of DNA recovered after four hours of incubation between FIG. 7 and FIG. 8 is likely due to the increased exposure to high heat and high humidity for the samples in FIG. 8.

Comparison of Repair Mixtures

Table 1, below, compares the ability of different enzyme combinations to effectively repair damaged DNA. The enzymes that were tested are Bst DNA Polymerase, T4 Endonuclease V, Endonuclease IV, Endonuclease VIII, DNA ligase, and uracil-DNA glycosylase (UDG). All enzymes were obtained from New England BioLabs Inc. and prepared according to the manufacturer's specifications including standard dilution in the supplied buffers. The DNA samples were the 113 bp full-length sequence of the DNA strand 500 from FIG. 5. Damage from long-term storage was simulated by exposing the DNA samples in solution to 70° C. and 50% RH for 24 hours.

Each sample was prepared by mixing 5 ng of DNA with 50 μL of ultrapure water in addition to a premix solution. The premix solution included 5 μL of ThermoPol® reaction buffer available from New England BioLabs, Inc. (catalog # B9004S), 0.5 μL of 10 mM dNTP mix, and 0.5 μL of 50 mM NAD$^+$. As used herein, "ultrapure water" refers to water having a purity such that resistivity is 18.2 MΩ·cm at 25° C. or "type 1" water as specified in ISO (International Organization for Standards) 3696. One source of ultrapure water is Milli-Q™ water available from Millipore Corporation.

The amount of DNA available after repair was measured by qPCR using the Roche LightCycler® 96.

The "undamaged" sample is a sample of the DNA strand that was not subjected to high heat and high humidity. Unsurprisingly, this sample has a much lower Cq value the any of the other samples. The "no repair" sample is a sample of DNA that was not incubated with a repair mixture. The Cq value this sample was 31.11. Thus, the Cq values lower than 31.11 indicate a benefit resulting from enzymatic repair. Values higher than 31.11 indicate that a repair mixture did not produce any benefit under these conditions.

The "control" sample is a sample of DNA incubated with the premix solution without any enzymes. The Cq value for the control sample of 27.59 is lower than the Cq values for many of the reaction mixtures that include enzymes. Without being bound by theory, it is believed that the success of the premix solution that repairing damage is an artifact present when dealing with very low DNA concentrations; similar benefits are not expected with higher DNA concentrations.

TABLE 1

Comparison of the ability of various enzyme combinations to repair damaged DNA.

| Sample | Bst Poly. | T4 Endo. V | Endo. IV | Endo. VIII | Ligase | UDG | Cq |
|---|---|---|---|---|---|---|---|
| Undamaged | n/a | n/a | n/a | n/a | n/a | n/a | 8.22 |
| No Repair | n/a | n/a | n/a | n/a | n/a | n/a | 31.11 |
| Control |  |  |  |  |  |  | 27.59 |
| 1 | x | x | x | x | x |  | 30.95 |
| 2 | x | x |  |  | x |  | 31.18 |
| 3 | x |  | x |  | x |  | 31.36 |
| 4 | x |  |  | x | x |  | 31.22 |
| 5 | x | x |  |  |  |  | 30.88 |
| 6 | x |  | x |  |  |  | 30.76 |
| 7 | x |  |  | x |  |  | 31.53 |
| 8 | x |  |  |  |  |  | 31.56 |
| 9 |  | x |  |  | x |  | 28.08 |
| 10 |  |  | x |  | x |  | 30.55 |
| 11 |  |  |  | x | x |  | 30.76 |
| 12 |  |  |  |  | x |  | 31.12 |
| 13 | x | x | x | x | x | x | 30.86 |
| 14 | x | x | x | x |  | x | 31.19 |
| 15 | x |  | x | x | x |  | 30.69 |
| 16 | x | x |  | x | x |  | 30.22 |
| 17 |  | x |  |  |  |  | 26.84 |
| 18 |  |  | x |  |  |  | 26.61 |

Surprisingly, the repair mixtures 17 and 18 which contain only single endonucleases, T4 Endonuclease V and Endonuclease IV respectively, performed better than repair mixtures with multiple enzymes. Without being bound by theory, it is believed that multiple enzymes may interfere with each other and reduce the ability to repair damaged DNA. While repair mixtures that include multiple enzymes may be useful for repairing damage to DNA strands that have suffered many different types of damage, if the DNA strands have been damaged in a uniform way, a mix of enzymes may decrease repair efficacy.

Table 2 compares the repair efficacy of repair mixtures with single endonucleases to the PreCR® Repair Mix. Two different length of DNA strands were tested: the 113 bp strand and the 53 bp strand introduced in FIG. 5. Sample preparation and testing was performed in the same manner as described above for the results shown in Table 1.

TABLE 2

Comparison of repair mixtures containing a single endonuclease with a commercial DNA repair mixture.

| T4 Endo V | Endo IV | Endo VIII | PreCR ® | Cq 53 bp | Cq 113 bp |
|---|---|---|---|---|---|
| x |  |  |  | 30.67 | 30.84 |
|  | x |  |  | 26.87 | 26.36 |
|  |  | x |  | 28.52 | 28.44 |
|  |  |  | x | 25.31 | 23.37 |

These comparisons show that the length of the DNA strand has a minor effect on the ability of the DNA to be repaired. Additionally, the combination of Taq DNA Ligase, Endonuclease IV, Bst DNA Polymerase, formamidopyrimidine DNA glycosylase (Fpg), Uracil-DNA Glycosylase, T4 Endonuclease V, and Endonuclease VIII in the PreCR® Repair Mix is more effective at repairing the damage to these DNA strands than either of the three endonucleases alone. However, the respective concentrations of the various enzymes in the PreCR® Repair Mix is not known, thus the difference may be due in part to variations in concentration rather than combination of enzymes used.

Table 3 compares the effects of enzyme concentration and incubation time on repair efficacy. The concentration of the PreCR® Repair Mix, the dNTPs in the buffer, and the NAD+ were used at the standard concentrations recommended by the manufacturer (indicated by "x") and at twice the recommended concentration (indicated by "xx"). The DNA samples were the 113 bp full-length sequence of the DNA strand 500 from FIG. 5. Damage from long-term storage was simulated by exposing the DNA samples in solution to 70° C. and 50% RH for 24 hours. The damaged DNA was incubated with the repair mixtures for either three, four, or five hours.

The "undamaged" sample is a sample of the DNA strand that was not subjected to high heat and high humidity. However, this sample may have some level of damage from short-term storage prior to testing. The "no repair" sample is a sample of DNA that was not incubated with a repair mixture. The Cq value this sample was 7.91. Thus, in this comparison Cq values lower than 7.91 indicate a benefit resulting from enzymatic repair.

TABLE 3

Comparison of enzyme concentrations and incubation time.

| Incubation Time | Sample | Cq | PreCR ® | dNTP | NAD+ |
|---|---|---|---|---|---|
| n/a | Undamaged | 6.28 | n/a | n/a | n/a |
|  | No Repair | 7.91 | n/a | n/a | n/a |
| 3 Hours | 1 | 7.54 | x | x | x |
|  | 2 | 7.01 | xx | x | x |
|  | 3 | 6.78 | xx | xx | x |
|  | 4 | 6.74 | xx | xx | xx |
| 4 Hours | 5 | 7.35 | x | x | x |
|  | 6 | 6.47 | xx | x | x |
|  | 7 | 6.04 | xx | xx | x |
|  | 8 | 6.33 | xx | xx | xx |
| 5 Hours | 9 | 6.72 | x | x | x |
|  | 10 | 6.64 | xx | x | x |
|  | 11 | 6.59 | xx | xx | x |
|  | 12 | 6.83 | xx | xx | xx |

All samples in this comparison showed improvement relative to the "no repair" sample. Incubation for four hours produced lower Cq values thus, higher DNA quantities, than incubation for three hours or for five hours. Doubling the concentration of the PreCR® Repair Mix to twice the level specified in the manufacturer's recommendations increased the amount of DNA that was able to be repaired. Doubling the amount of dNTPs also increased repair efficacy. However, doubling the amount of NAD$^+$ had the opposite effect.

The best result, sample number 7 with a Cq value of 6.04, was achieved with double the standard amount of PreCR® Repair Mix and double the amount of dNTPs. This is a lower Cq value for that than the undamaged sample indicating that there may be some level damage present even without exposure to high heat and high humidity and this damage is repaired by this repair mixture.

ILLUSTRATIVE EMBODIMENTS

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method of storing digital information in deoxyribose nucleic acid (DNA) comprising: encoding the digital information as a sequence of nucleotides; synthesizing a synthetic DNA molecule having the sequence of nucleotides; storing the synthetic DNA molecule; contacting the synthetic DNA molecule with a repair mixture comprising at least one of a DNA polymerase, a DNA ligase, or an endonuclease; sequencing the synthetic DNA molecule following the contacting with the repair mixture to generate sequence data; and decoding the sequence data to obtain regenerated digital information.

Clause 2. The method of clause 1, wherein the encoding the digital information uses an encoding schema that includes error correction.

Clause 3. The method of clause 1 or 2, wherein the synthesizing the synthetic DNA molecule is performed by an oligonucleotide synthesizer and the DNA molecule is between approximately 100-180 base pairs (bp) long.

Clause 4. The method of any of clauses 1-3, wherein the contacting the synthetic DNA molecule with the repair mixture is performed for approximately 4 hours at approximately 37° C.

Clause 5. The method of any of clauses 1-4, wherein, subsequent to the synthesizing the synthetic DNA molecule, the synthetic DNA molecule is maintained at a temperature of no greater than approximately 25° C. until the contacting the synthetic DNA molecule with the repair mixture.

Clause 6. The method of any of clauses 1-5, wherein the repair mixture comprises Bst DNA polymerase.

Clause 7. The method of any of clauses 1-6, wherein the repair mixture comprises Taq DNA ligase.

Clause 8. The method of any of clauses 1-7, wherein the repair mixture comprises at least one of T4 Endonuclease V, Endonuclease IV, or Endonuclease VIII.

Clause 9. A method of repairing synthetic DNA encoding digital information comprising: contacting the synthetic DNA with a repair mixture comprising at least one of a DNA polymerase, a DNA ligase, or an endonuclease; and amplifying the synthetic DNA by polymerase chain reaction (PCR), wherein PCR amplification of the synthetic DNA following the contacting with the repair mixture reduces the Cq cycle count by at least 1.5 compared to PCR amplification of the synthetic DNA without contacting with the repair mixture.

Clause 10. The method of clause 9, wherein the synthetic DNA has a length of approximately 100-180 bp and is synthesized by an oligonucleotide synthesizer according to a predetermined encoding of the digital information.

Clause 11. The method of clause 9 or 10, wherein the contacting the synthetic DNA with the repair mixture is performed for approximately 4 hours at approximately 37° C.

Clause 12. The method of any of clauses 9-11, wherein the repair mixture comprises at least one of Bst DNA polymerase, Taq DNA ligase, Endonuclease IV, T4 Endonuclease V, or Endonuclease VIII.

Clause 13. The method of any of clauses 9-12, wherein the repair mixture comprises Bst DNA polymerase, Taq DNA ligase, Endonuclease IV, T4 Endonuclease V, and Endonuclease VIII.

Clause 14. The method of any of clauses 9-13, wherein the repair mixture consists essentially of T4 Endonuclease V.

Clause 15. The method of any of clauses 9-13, wherein the repair mixture consists essentially of Endonuclease IV.

Clause 16. The method of any of clauses 9-15, wherein PCR amplification of the synthetic DNA following the contacting with the repair mixture reduces the Cq cycle count by at least 2.0 compared to PCR amplification of the synthetic DNA without contacting with the repair mixture.

Clause 17. The method of any of clauses 9-16, further comprising sequencing the synthetic DNA following the PCR amplification.

Clause 18. A method of recovering digital information stored in synthetic DNA comprising: determining that a quantity of intact DNA strands in the synthetic DNA is less than a threshold level; contacting the synthetic DNA with a repair mixture comprising at least one of a DNA polymerase, a DNA ligase, or an endonuclease; and sequencing the synthetic DNA to generate sequence data.

Clause 19. The method of clause 18, wherein the threshold level is based on a difference between a Cq value for the synthetic DNA prior to storage and a Cq value for the synthetic DNA after storage.

Clause 20. The method of clause 18 or 19, further comprising decoding the sequence data to obtain regenerated digital information.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention (especially in the context of the following claims) are to be construed to cover both the singular and the plural, unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications (collectively "references") throughout this specification. Each of the cited references is individually incorporated herein by reference for its particular cited teachings as well as for all that they disclose.

The invention claimed is:

1. A method of increasing a quantity of PCR-amplifiable synthetic double-stranded DNA comprising natural bases encoding digital information, the method comprising:
   determining that the quantity of PCR-amplifiable DNA in the synthetic double-stranded DNA is less than a threshold level, wherein the threshold level is based on a change in the quantity of PCR-amplifiable DNA before and after storage as measured by quantitative PCR;
   contacting the synthetic double-stranded DNA with a repair mixture comprising an endonuclease; and
   amplifying the synthetic double-stranded DNA by polymerase chain reaction (PCR).

2. The method of claim 1, wherein the synthetic double-stranded DNA has a length of approximately 100-180 bp and is synthesized by an oligonucleotide synthesizer according to a predetermined encoding of the digital information.

3. The method of claim 2, wherein the predetermined encoding of the digital information uses an encoding schema that includes error correction.

4. The method of claim 1, wherein the repair mixture further comprises at least one of Bst DNA polymerase, Taq DNA ligase, formamidopyrimidine DNA glycosylase (Fpg), or uracil-DNA Glycosylase (UDG).

5. The method of claim 4, wherein the endonuclease is selected from Endonuclease IV, T4 Endonuclease V, and Endonuclease VIII.

6. The method of claim 1, wherein the repair mixture comprises Bst DNA polymerase, Taq DNA ligase, Endonuclease IV, T4 Endonuclease V, Endonuclease VIII, formamidopyrimidine DNA glycosylase (Fpg), and uracil-DNA Glycosylase (UDG).

7. The method of claim 1, further comprising sequencing the synthetic double-stranded DNA following the PCR amplification.

8. The method of claim 7, further comprising decoding a sequence of the synthetic double-stranded DNA generated by the sequencing to obtain digital information.

9. The method of claim 1, wherein the repair mixture further comprises a DNA polymerase and wherein the DNA polymerase is Bst DNA polymerase.

10. The method of claim 1, wherein the repair mixture further comprises a DNA ligase and wherein the DNA ligase is Taq DNA ligase.

11. The method of claim 1, wherein the endonuclease is Endonuclease IV, T4 Endonuclease V, or Endonuclease VIII.

12. The method of claim 11, wherein the repair mixture comprises multiple endonucleases and wherein the multiple endonucleases comprise Endonuclease IV, T4 Endonuclease V, and Endonuclease VIII.

13. The method of claim 1, wherein the repair mixture further comprises a glycosylase and wherein the glycosylase is formamidopyrimidine DNA glycosylase (Fpg) or uracil-DNA Glycosylase (UDG).

14. The method of claim 13, wherein the repair mixture further comprises multiple glycosylases and wherein the multiple glycosylases comprise formamidopyrimidine DNA glycosylase (Fpg) and uracil-DNA Glycosylase (UDG).

15. The method of claim 1, wherein contacting the synthetic double-stranded DNA with the repair mixture is performed for approximately 4 hours at approximately 37° C.

16. The method of claim 1, wherein the change in the quantity of PCR-amplifiable DNA is determined by comparing a first quantity of PCR-amplifiable DNA which is measured before storage and is represented by a first Cq value to a second quantity of PCR-amplifiable DNA which is measured after storage and is represented by a second Cq value.

17. The method of claim 16, wherein the threshold level is a numerical difference between the first Cq value and the second Cq value or the threshold level is based on a quantity of DNA needed to successfully recover the digital information.

18. The method of claim 1, wherein the repair mixture comprises the endonuclease and at least one of a DNA polymerase, a DNA ligase, or a glycosylase.

19. The method of claim 18, wherein the repair mixture comprises the endonuclease and at least two of a DNA polymerase, a DNA ligase, or a glycosylase.

20. The method of claim 19, wherein the repair mixture comprises the endonuclease, a DNA polymerase, a DNA ligase, and a glycosylase.

* * * * *

SEQUENCE LISTING

```
<160> NUMBER OF SEQ ID NOS: 6

<210> SEQ ID NO 1
<211> LENGTH: 113
<212> TYPE: DNA
<213> ORGANISM: Artificial Sequence
<220> FEATURE:
<223> OTHER INFORMATION: synthetic sequence for illustrative purposes

<400> SEQUENCE: 1
atcgggttac actggctgac acttattctt caggtaagga ccccttattg gcagtggtga      60
gtgaggtttg gcactatccc tactactgat ggtcttaccc ctgtcgcatg aat            113

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
atcgggttac actggctgac                                                  20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
attcatgcga caggggtaag                                                  20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ctgacactta ttcttcaggt                                                  20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gtaagaccat cagtagtagg                                                  20
```

```
<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
aacctcactc accactgcca                                                  20
```